United States Patent
Klein et al.

(10) Patent No.: US 7,327,448 B2
(45) Date of Patent: Feb. 5, 2008

(54) LASER-ULTRASONIC DETECTION OF FLIP CHIP ATTACHMENT DEFECTS

(75) Inventors: Marvin Klein, Pacific Palisades, CA (US); Todd Murray, Roslindale, MA (US)

(73) Assignees: Optech Ventures LLC, Torrance, CA (US); Boston University, Boston, MA (US)

( * ) Notice: Subject to any disclaimer, the term of this patent is extended or adjusted under 35 U.S.C. 154(b) by 196 days.

(21) Appl. No.: 10/903,557

(22) Filed: Jul. 29, 2004

(65) Prior Publication Data

US 2006/0021438 A1    Feb. 2, 2006

(51) Int. Cl.
*G01N 21/88* (2006.01)
(52) U.S. Cl. .................... 356/237.1; 356/502
(58) Field of Classification Search ........ 356/506, 356/237.1, 357, 432, 351–352; 438/14, 16; 257/778
See application file for complete search history.

(56) References Cited

U.S. PATENT DOCUMENTS

| | | | |
|---|---|---|---|
| 5,585,921 A * | 12/1996 | Pepper et al. | 356/487 |
| 6,747,268 B1 * | 6/2004 | Ume | 250/227.11 |
| 2005/0225754 A1 * | 10/2005 | Ume et al. | 356/237.1 |

* cited by examiner

*Primary Examiner*—Zandra V. Smith
*Assistant Examiner*—Tsz Chiu
(74) *Attorney, Agent, or Firm*—D. Morgan Tench

(57) ABSTRACT

Underfill voids and solder ball defects are detected via laser generation and laser detection of an ultrasonic wave at the top surface of flip chips. High resolution is provided by using small laser spot sizes and closely-spaced laser beams of wavelengths that are absorbed near the surface of the semiconductor. Alternatively, the generation laser beam may be absorbed in the bulk of the semiconductor. Improved spatial resolution and rejection of unwanted scattered waves can be attained by limiting the time frame of the ultrasonic waveform to the time required for the first longitudinal wave reflection from the bottom of the flip chip. The laser beam spacing can be reduced by using overlapping probe and detection beams of different wavelengths. Resolution of less than 100 μm features was demonstrated for silicon flip chips.

19 Claims, 4 Drawing Sheets

LASER-ULTRASONIC DETECTION OF FLIP CHIP ATTACHMENT DEFECTS

U.S. GOVERNMENT RIGHTS

This invention was made with Government support under Contract No. DTRA01-03-C-0030 awarded by the Missile Defense Agency. The Government has certain rights in this invention.

BACKGROUND OF THE INVENTION

1. Field of the Invention

The present invention is generally related to electronics assembly and is more specifically concerned with quality control of flip chip attachment.

2. Description of the Related Art

Modern electronic assemblies generally contain integrated circuits and digital memory incorporated in semiconductor chips. In early approaches, chips were mounted and contacted electrically via wire bonds running from metallic contact pads around the periphery of the top side of the chip to mating pads on a polymer-based or ceramic chip carrier or substrate. The carrier and chip were typically contained in a package that protected the chip, and had solderable leads for attachment to a circuit board. Later approaches involved wire bonding the chip directly to pads on a circuit board so as to eliminate the package and reduce the footprint of the device. As electronics miniaturization progressed, chips become so small and densely packed with circuitry and circuit elements that even fine-pitched peripheral contacts could no longer provide the needed number of input/output (I/O) connections. Furthermore, wire bond connections introduced appreciable inductive impedance, which limited the device switching speed. These issues were addressed by distributing the electrical contact pads in an area array over one side of the chip, and making electrical contacts via short solder connections.

In the flip chip approach, solder balls are first attached to an array of contact pads distributed over the "top" or active surface of the chip to form a solder ball array. The chip is then flipped upside down and positioned so that the solder balls are aligned with mating contact pads on the substrate, which is typically a polymer-based or ceramic circuit board. The solder interconnections are made by reflow soldering. The empty space between the bottom of the flip chip and the substrate is generally filled with an epoxy underfill material to reduce thermally-induced strain that could cause fatigue cracking of the solder interconnections. For some applications, underfill is also required for heat removal and to provide resistance to acceleration-induced strain. The underfill material, which is typically a proprietary epoxy formulation, is generally injected as a liquid so that air bubbles sometimes produce underfill voids that can cause localized heating/stresses, leading to premature failure. The solder connections may also have inadequate electrical or mechanical properties due to voids, disbonds or insufficient solder ball volume. A means for controlling such underfill and solder defects is needed to improve process yields and to ensure high reliability for critical applications.

The only practical prior art technique for detecting underfill voids is scanning acoustic microscopy, which requires that the part be immersed in water (or another fluid). This technique can be applied only after the epoxy underfill has cured, which precludes reworking the part since the cured epoxy cannot be removed without damaging the chip. Water immersion of the part is also incompatible with in-line inspection so that only a small fraction of the parts can be tested, which provides only statistical process control. A method enabling in-line detection of flip chip attachment defects would provide great benefits in terms of part reliability and process yields.

U.S. Pat. No. 5,585,921 to Pepper et al. describes a laser-ultrasonic system applied to on-line detection of welding defects. In this case, one laser was used to generate an array of acoustic waves within the workpiece and a second laser, coupled with an interferometer, was used to detect vibrations of the workpiece surface produced by the laser-generated acoustic waves. The magnitude of the measured acoustic waves was increased via reflections from incompletely formed welds. The array of acoustic waves was generated and detected via full or partial concentric ring-shaped laser beams designed so that the component waves arrived at the detection site at the same time and were reflected in-phase. This focused the ultrasonic energy on the weld area, enhancing the signal strength and reducing the effects of speckle reflections from rough weld surfaces. Nonetheless, the width of the focus area even with the acoustic wave array was about 1 mm, which is an order of magnitude larger than the resolution needed for detection of flip chip attachment flaws (<100 µm). Such prior art implies that the laser-ultrasonic approach may not be applicable to the flip chip application.

Pepper et al. (Rev. Prog. Quant. NDE, Vol. 17, Plenum Press, New York, 1998) describe void detection in a flip chip package via a laser-ultrasonic technique involving ultrasonic generation on the polymer-based substrate (FR4 material) and detection on the opposite side of the package, i.e., at the top surface of the flip chip. The generation laser employed had a relatively large spot size (~0.5 mm diameter), which enhanced ultrasonic wave generation with minimal laser-induced damage to the substrate but severely limited the attainable resolution. Nonetheless, the laser power used exceeded the ablation threshold of the FR4 substrate material, rendering the technique partially destructive. Since this prior art approach provided limited resolution, relatively large laser scanning steps (100 µm) were used.

SUMMARY OF THE INVENTION

The present invention provides a laser-ultrasonic method and device that are useful for detection of defects in the underfill and solder ball attachments between a flip chip and a substrate. In the method of the invention, a probe acoustic wave is generated in the flip chip by directing a generation laser beam of small diameter to a predetermined generation spot on the top surface of the flip chip. The acoustic bandwidth may be maximized by using a generation laser of a wavelength that is strongly absorbed by the flip chip semiconductor so that the laser light is absorbed in a thin region near the top surface of the flip chip. Alternatively, the wavelength of the generation laser light may be selected so as to distribute the light absorption over a greater volume of the semiconductor to enhance the directivity and intensity of the acoustic wave while avoiding ablation damage to the flip chip. The ultrasonic wave reflected from the bottom surface of the chip, whose intensity is modulated by a void in the underfill or a defect in a solder ball, is detected via the temporal displacement of the top surface of the flip chip produced by the reflected acoustic wave. This surface displacement is measured using an interferometer and a detection laser beam of small diameter that impinges the top surface of the flip chip at a detection spot. The detection laser beam preferably has a wavelength that is strongly absorbed by the flip chip semiconductor so that it efficiently senses the motion of the flip chip top surface (laser entrance face).

In a preferred embodiment, high sensitivity and resolution are attained via use of very small laser spot diameters and a close spacing between the generation laser spot and the detection laser spot. In this case, only those ultrasonic waves that travel in a narrow angular range, defining a small probe area at the bottom surface of the chip, are detected so that very small voids and defects can be resolved. For the thin silicon chips normally employed, features smaller than the wavelength of the generated ultrasonic wave can be resolved. The generation laser spot and the detection laser spot may overlap if lasers of two different wavelengths are used.

The detection of the reflected ultrasonic wave may be time gated so that waves arriving at longer or shorter times compared to those for a predetermined time range are not detected. Thus, reflected ultrasonic waves that must travel a shorter or longer distance to arrive at the detection spot (compared to those from the defined probe area) are rejected. This approach provides further spatial selectivity for the waves reflected from the defect location being probed, and enables rejection of non-specular reflections from areas outside the probe area for flip chips with scattering features at the bottom surface.

The method of the invention may be used to provide an image of underfill and solder ball defects. In this case, measurements of acoustic waveforms (surface displacement magnitude vs. time) are made at regularly spaced locations along the flip chip surface by x-y raster scanning of the laser beams or the flip chip, while a predetermined spatial relationship is maintained between the generation laser spot and the detection laser spot. Enhanced resolution and sensitivity may be provided via more sophisticated signal processing.

In a preferred embodiment, a single waveform corresponding to a defect-free location is chosen as a reference, and the overall amplitude of each waveform is normalized to the amplitude of the reference waveform. The time frame considered for the normalized waveforms is preferably gated to the arrival time of the first longitudinal wave reflection from the probe area at the bottom surface of the flip chip. A computer program is preferably used to calculate the Mean Square Error (MSE) between the reference waveform and each of the other waveforms in the raster scan. A plot of MSE intensity versus x-y location provides an image of the bottom side of the flip chip.

The device of the present invention for detecting a defect in an attachment between a flip chip and a substrate comprises a generation laser, a detection laser, an interferometer and an analyzer, and may further comprise a translation stage.

The present invention provides significant advantages compared to prior art methods. A key advantage is that the laser-ultrasonic method and device of the invention can be used for in-line detection of flip chip attachment defects, enabling 100% parts inspection and real-time process control. Since fluid immersion is not required, laser-ultrasonic inspection can be applied before the epoxy underfill has cured so that defective parts can be reworked when necessary. The present invention also provides high defect sensitivity and resolution. For the thin semiconductor layers typically employed for flip chips, attachment defects smaller than the wavelength of the laser-generated ultrasonic wave can be detected. The present invention may be used to improve the reliability of flip chip parts and increase the yield of flip chip assembly processes.

Further features and advantages of the invention will be apparent to those skilled in the art from the following detailed description, taken together with the accompanying drawings.

These figures are not drawn to scale. Some features have been enlarged relative to other features for ease of depiction.

DETAILED DESCRIPTION OF THE INVENTION

The present invention provides a laser-ultrasonic method and device that are useful for detection of defects in the underfill and solder ball attachments between a flip chip and a substrate. A flip chip includes an area array of solder balls between contact pads on the flip chip and contact pads on the substrate. The solder ball attachment is typically made by reflow soldering. The substrate may comprise any polymer-based material, FR4 material, for example, or any ceramic material, alumina, for example. The present invention may be applied to detection of attachment defects for flip chips comprising any semiconductor material, including silicon, germanium, gallium arsenide, indium phosphide, and silicon carbide. Attachment defects that may be detected include underfill voids, underfill disbonds, missing solder balls, disbanded solder balls, and solder balls with insufficient solder mass.

In this document, the term "flip chip" is used in the broadest sense and includes any semiconductor chip having an area array of electrical contacts on one surface. Thus, the term "flip chip" encompasses chips in chip scale packages, which may be contacted to a circuit board via a flex circuit and solder balls or bumps. The words "acoustic" and "ultrasonic" are used interchangeably.

Figure 1:
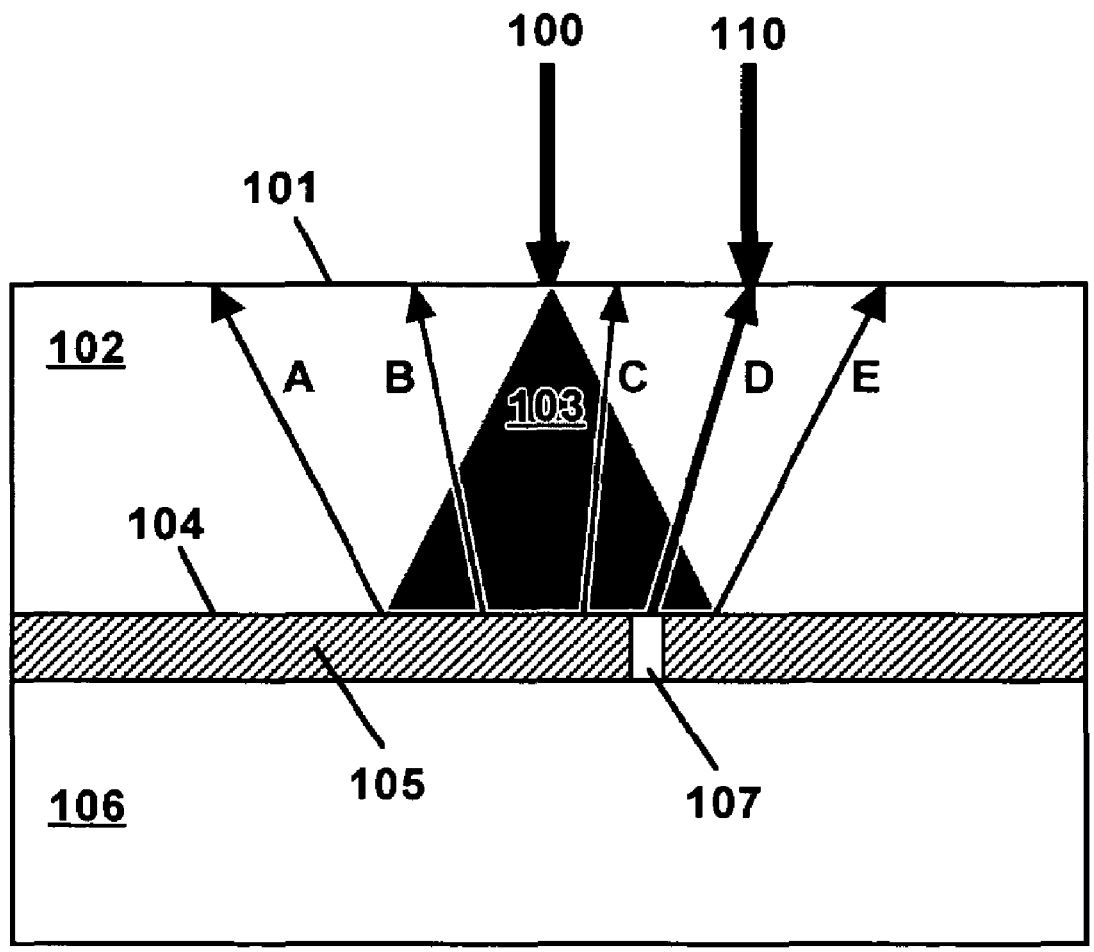
FIG. 1 is a schematic cross-section that illustrates laser-ultrasonic detection of an attachment defect for a flip chip having a smooth bottom surface for which reflection of ultrasonic waves is specular.

FIG. 1 illustrates the method of the present invention for detection of an attachment defect for a flip chip having a substantially smooth bottom surface for which reflection of the laser-generated ultrasonic wave is specular. Note that the flip chip surface may include circuitry lines and devices but these are usually smaller than the desired resolution and are not detected. Generation laser beam 100 incident at a generation spot on top surface 101 of flip chip 102 generates an ultrasonic wave 103 (in flip chip 102) that diverges from the generation spot and is specularly reflected from smooth bottom surface 104 of flip chip 102. Bottom surface 104 is in contact with underfill 105 between flip chip 102 and substrate 106. Ultrasonic wave D reflected from bottom flip chip surface 104 within a small probe area (not shown) impinges a detection spot on top surface 101, defined by detection laser beam 110, and causes a localized temporal displacement of surface 101. A portion of detection laser beam 110 reflected from surface 101 is analyzed via an interferometer to generate an acoustic waveform for ultrasonic wave D. When, as in FIG. 1, the probe area fully or partially overlaps a defect in underfill 105, such as void 107, the intensity of the acoustic waveform is typically enhanced. Void 107 is detected by comparing the acoustic waveforms for a plurality of generation and detection spots on top surface 101 of flip chip 102. Since the angle of reflectance from bottom surface 104 for an ultrasonic wave generated by generation laser beam 100 equals the angle of incidence, ultrasonic waves A, B, C and E reflected from areas of bottom surface 104 outside the probe area do not impinge the detection spot and are not detected. This enhances the signal to noise ratio so that high spatial sensitivity can be attained. Thus, the present invention permits interrogation of a small probe area at the bottom surface of a flip chip via ultrasonic waves traveling in a narrow spatial and angular range defined by the flip chip thickness and the spacing and spot diameters of the generation and detection laser beams.

For prior art laser-ultrasonic detection methods, attainable resolution is limited by divergence of the generated ultrasonic wave, and by the relatively large probe areas typically involved. We have discovered, however, that very small flip chip attachment defects can be detected by generating and detecting the ultrasonic wave on the top surface of the flip chip using closely-spaced laser beams of small spot diameters. This contrasts with the prior art approach for laser-ultrasonic inspection of flip chips via generation and detection on opposite sides of the flip chip (D. M. Pepper, G. J. Dunning, M. P. Chiao, T. R. O'Meara and P. V. Mitchell, Rev. Prog. Quant. NDE, Vol. 17, Plenum Press, New York, 1998).

With generation and detection on top flip chip surface 101 (FIG. 1), according to the present invention, divergence of ultrasonic wave 103 is minimized since the generated and reflected waves must traverse only the thickness of flip chip 102. Since the thickness of flip chip 102 is typically very small (<1 mm), practically the full intensity of laser-generated ultrasonic wave 103 is delivered to bottom surface 104. This maximizes the intensity of reflected ultrasonic wave D and the strength of the signal detected via detection laser beam 110. In this case, attainable resolution is limited by the spacing and spot sizes of the laser beams and the signal processing efficiency, and not by the wavelength of the ultrasonic wave. For closely-spaced laser beams of small spot diameter, we have shown that the dimensions of the probe area for reflected ultrasonic beam 107 can be much smaller than the wavelength of the highest frequency ultrasonic wave.

The method of the present invention for detecting a defect in an attachment between a flip chip and a substrate comprises the steps of: (1) generating a probe acoustic wave within the flip chip by directing a generation laser beam to a predetermined generation spot on the top surface of the flip chip; (2) detecting a reflected acoustic waveform via an interferometer and a detection laser beam that impinges the top surface of the flip chip at a detection spot having a predetermined spatial relationship to the generation spot; (3) repeating steps (1) and (2) for a plurality of predetermined generation and detection spots on the top surface of the flip chip; and (4) comparing the reflected acoustic waveforms detected for at least two predetermined detection spots to detect the defect in the attachment between the flip chip and the substrate.

The generation laser beam preferably comprises a single pulse so as to provide maximum ultrasonic wave amplitude without substantial damage to the flip chip. Multiple generation laser pulses could be used. The generation laser pulse energy is preferably below the ablation threshold, which depends on the semiconductor material and the wavelength of the laser light. In the thermoelastic regime below the ablation threshold, the laser beam generates two types of acoustic waves that may be used to interrogate the flip chip bottom surface. Compressional waves, which are relatively weak and travel primarily along the normal to the flip chip surface, can only be detected when the generation and detection laser beams are very close together, preferably overlapped. The pulse width of compressional waves is limited only by the temporal width of the laser pulse. Shear waves, which are relatively strong, tend to travel at angles to the surface normal. The pulse width of shear waves is also limited only by the temporal width of the laser pulse, provided that the generation laser spot size is sufficiently small.

The wavelength of the generation laser beam is preferably predetermined such that the generation laser light is absorbed in a relatively thin region near the top surface of the flip chip. When the photon energy of the generation laser exceeds the bandgap energy of the semiconductor material comprising the flip chip, the laser light is absorbed in a very thin region near the flip chip top surface, which maximizes the acoustic bandwidth. Especially for a semiconductor material that has an indirect bandgap, such as silicon, a sub-bandgap laser photon energy may be employed to distribute the light absorption over a greater volume in the bulk of the semiconductor so as to enhance the directivity and intensity of the acoustic wave while avoiding ablation damage to the flip chip. The photon energy of the detection laser is preferably predetermined to exceed the bandgap energy of the semiconductor so that light penetration is minimized, providing good sensitivity to temporal displacement of the top surface. Note that even a strongly absorbing material has an intrinsic Fresnel reflectivity, enabling laser-interferometer detection of the top surface displacement.

The sensitivity and resolution provided by the invention are enhanced by use of small laser spot sizes and a close spacing between the generation and detection laser spots. The spot diameter for both the generation and detection laser beams should be as small as practical, preferably 100 μm or less. The center-to-center spacing between the generation and detection laser spots should be less than 300 μm. If the generation and detection laser beams have different wavelengths, the generation and detection spots may be overlapped to increase signal strength and improve the signal-to-noise ratio.

The ultrasonic wave reflected from the bottom surface of the chip, whose intensity is modulated by a void in the underfill or a defect in a solder ball, is detected via the temporal displacement of the top surface of the flip chip produced by the reflected acoustic wave. This surface displacement is measured using an interferometer and a detection laser beam of small diameter that impinges the top surface of the flip chip at a detection spot. Suitable interferometer-laser vibration detection equipment and methods are known in the art. A preferred detection scheme involves the use of two-wave mixing in a photorefractive crystal. The crystal acts as an adaptive beam combiner, allowing interrogation of rough surfaces and avoiding the need for any path-length stabilization in the interferometer.

For silicon flip chips, 532-nm light, which may be provided by a frequency-doubled Nd:YAG laser, may be used for both generation and detection. Such above-bandgap light is absorbed within about 0.1 μm into the silicon surface, providing high acoustic bandwidth. Alternatively, 1064 nm light, which may be provided by a fundamental Nd:YAG laser, may be used for acoustic wave generation in silicon. Such near-bandgap light penetrates to a depth of about 200 μm into the silicon bulk. Since absorption of 1064-nm light is distributed over a relatively large silicon volume (compared to 532-nm light), a laser pulse of higher energy may be used to enhance ultrasonic wave generation without exceeding the ablation threshold. The buried nature of 1064-nm absorption in silicon and the resulting mechanical clamping ensure that strong compressional ultrasonic waves are produced, with a peak directivity along the normal to the surface. The distributed nature of the 1064-nm absorption, however, leads to time broadening of the propagating ultrasonic pulse, thereby reducing its bandwidth. The reduced bandwidth in turn leads to acoustic waves of longer wavelength, which can still be used to detect small flip chip attachment defects. Overlap of the generation and detection beams to enhance resolution for silicon chips may be provided by using 532-nm light for generation and 515-nm light for detection.

Within the scope of the present invention, signal-to-noise ratio may be enhanced by utilizing a predetermined time frame for the waveforms corresponding to the arrival time of the first longitudinal wave reflected from the bottom surface of the chip. This time gating approach effectively rejects contributions from ultrasonic waves reflected outside the probe area, which must traverse a greater or smaller distance and arrive at the detection spot at times outside the predetermined time frame.

Figure 2:
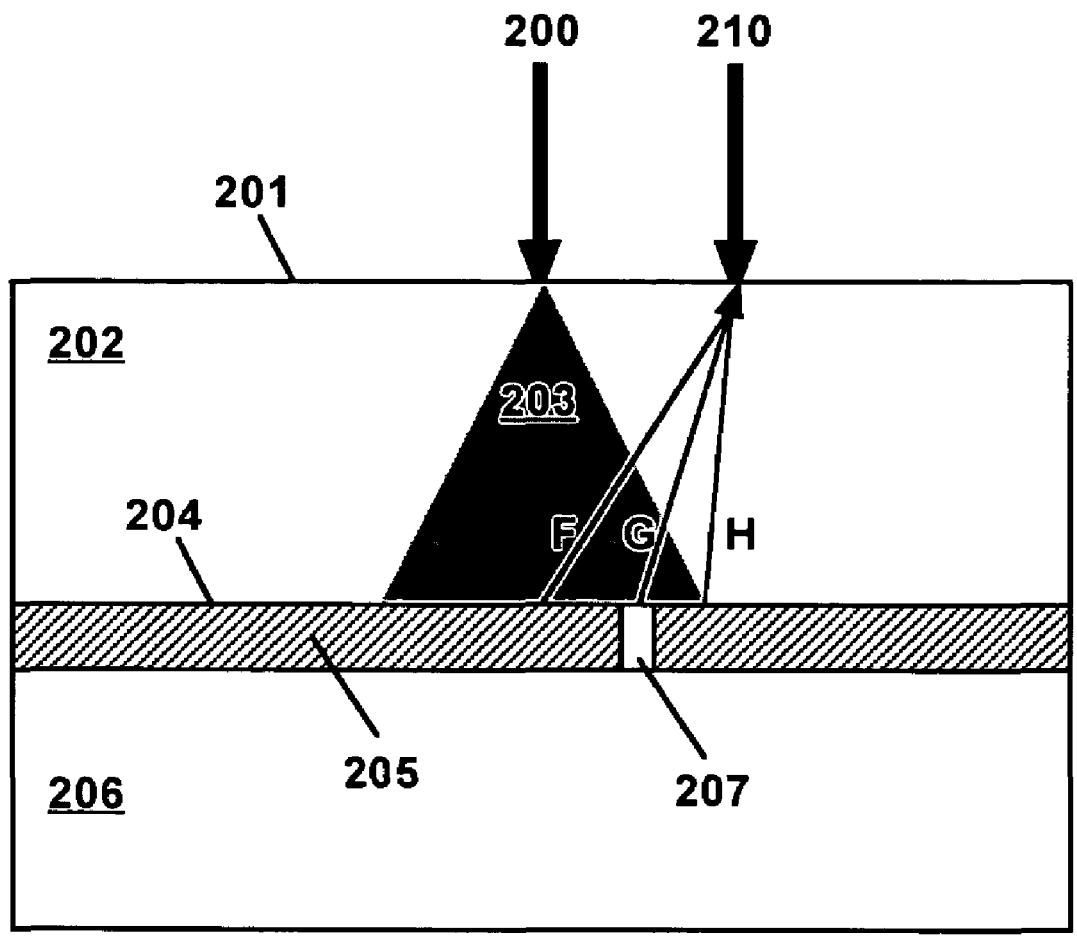
FIG. 2 is a schematic cross-section that illustrates laser-ultrasonic detection of an attachment defect for a flip chip having scattering features at the bottom surface so that the reflection of ultrasonic waves is non-specular.

FIG. 2 illustrates application of the method of the present invention to detection of an attachment defect for a flip chip having scattering features at the bottom surface, which may be associated with integrated circuit conductor lines or electronic devices, for example. Generation laser beam 200 incident at a generation spot on top surface 201 of flip chip 202 generates an ultrasonic wave 203 (in flip chip 202) that is reflected or scattered from bottom surface 204, which is in contact with underfill 205 between flip chip 202 and substrate 206. Ultrasonic wave G reflected from bottom flip chip surface 204 within a small probe area (not shown) impinges a detection spot on top surface 201, defined by detection laser beam 210. Since scattering of acoustic waves from scattering features at bottom surface 204 occurs over a range of angles, ultrasonic waves F and H reflected from bottom surface 204 outside the probe area also impinge the detection spot on top surface 201 (defined by laser beam 210) and are detected as false signals. However, the distance to the detection spot for waves F and H are longer and shorter, respectively, compared to the signal wave G. Thus, the false signals from waves F and H can be eliminated by time gating with respect to the signal wave G, i.e., rejecting waves arriving at the detection spot at shorter or longer times compared to signal wave G. Time gating also tends to enhance the spatial resolution for defect detection.

In a preferred embodiment, a single waveform corresponding to a defect-free location is chosen as a reference, and the overall amplitude of each waveform is normalized to the amplitude of the reference waveform. The normalized waveforms are preferably time gated at the arrival time of the first longitudinal wave reflected from the bottom surface of the chip. A computer program is preferably used to calculate the Mean Square Error (MSE) between the reference waveform and each of the other waveforms in the raster scan. The MSE values are used as a measure of the defect scattering level. A plot of MSE intensity versus x-y location provides an image of the bottom side of the flip chip.

The device of the present invention for detecting a defect in an attachment between a flip chip and a substrate comprises a generation laser, a detection laser, an interferometer and an analyzer, and may further comprise a translation stage. The generation laser provides a generation laser beam that impinges the top surface of the flip chip at a predetermined generation spot and generates an acoustic wave within the flip chip. The detection laser provides a detection laser beam that impinges the top surface of the flip chip at a detection spot having a predetermined spatial relationship to the predetermined generation spot. The interferometer provides an acoustic waveform of the temporal displacement of the top surface of the flip chip at the detection spot based on the magnitude of a portion of the detection laser beam reflected from the top surface of the flip chip. The analyzer compares a plurality of the acoustic waveforms to detect the defect in the attachment between the flip chip and the substrate. The translation stage x-y raster scans the flip chip top surface relative to the generation and detection laser spots while acoustic waveforms are measured at predetermined locations along the flip chip top surface to provide an image of attachment defects at the bottom surface of the flip chip.

DESCRIPTION OF A PREFERRED EMBODIMENT

The efficacy of the present invention was demonstrated by generating a laser-ultrasonic images of an underfill void and missing solder balls for silicon flip chips (<600 μm thick) attached to an FR4 substrate. A single waveform corresponding to a defect-free location was chosen as a reference, and the overall amplitude of each waveform was normalized to the amplitude of the reference waveform. The time frame considered for the normalized waveforms was then gated to the arrival time of the first longitudinal wave reflection from the probe area at the bottom surface of the flip chip. A computer program was used to calculate the Mean Square Error (MSE) between the reference waveform and each of the other waveforms in the raster scan. A plot of MSE intensity versus x-y location provided an image of the bottom side of the flip chip.

Figure 3:
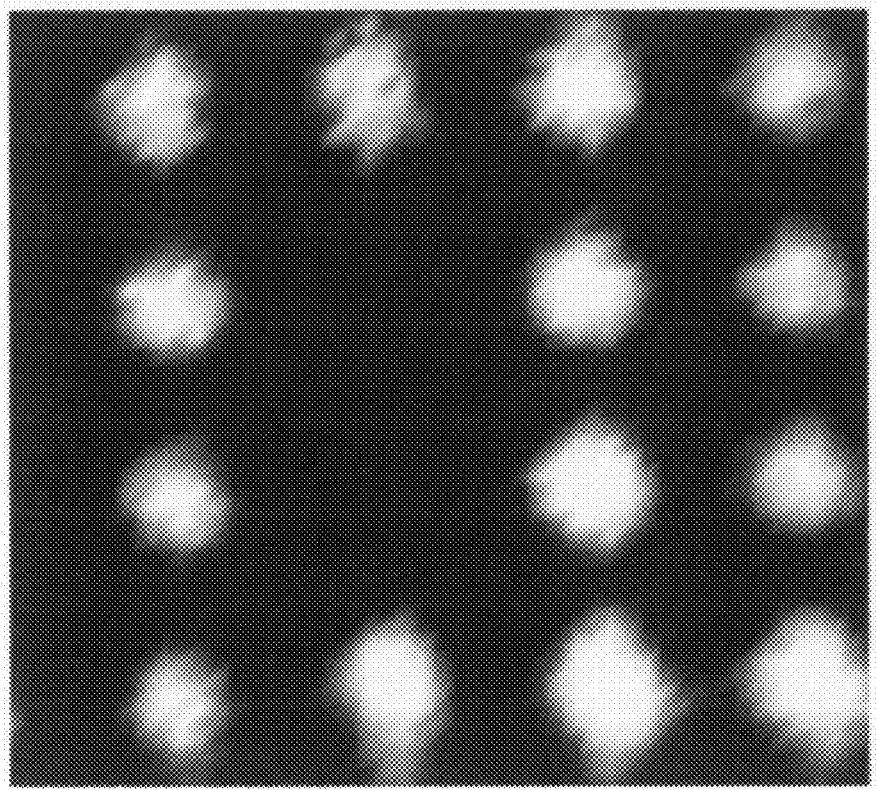
FIG. 3 shows an image of a chip scale package solder bump array with missing solder balls generated by the laser-ultrasonic method of the present invention.

FIG. 3 shows an image of a chip scale package solder ball array generated by the laser-ultrasonic method of the present invention. The solder balls were 435 μm in diameter and the pitch of the array was 750 μm. Ultrasonic wave generation was provided by a 532-nm doubled Nd:YAG laser (0.64 mJ/pulse) with a 100 μm spot size. The detection laser had a wavelength of 515 nm, a spot size of 100 μm, and a power output of 50 mW. Acoustic waveforms of surface displacement magnitude vs. time were measured at 60-μm steps along the flip chip surface by x-y raster scanning. The generation and detection laser spots were overlapped on the top surface. The scan area was 3 mm×3 mm in size. Two missing solder balls are clearly evident.

Figure 4:
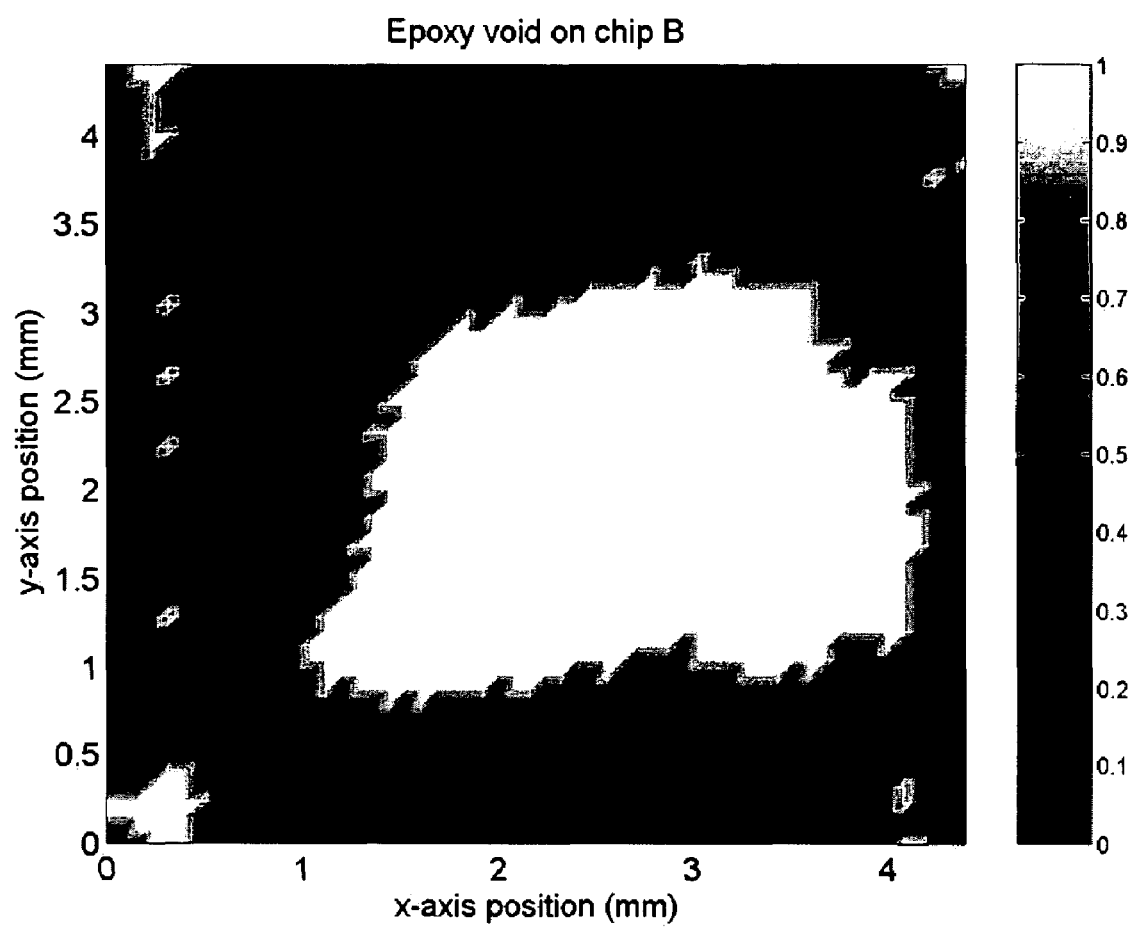
FIG. 4 shows an image of a flip chip underfill void generated by the laser-ultrasonic method of the present invention.

FIG. 4 shows an image of a flip chip underfill void generated by the laser-ultrasonic method of the present invention. The solder balls were 135 μm in diameter and the pitch of the array was 254 μm. Ultrasonic wave generation was provided by a 1064-nm Nd:YAG laser (4.37 mJ/pulse) with a 100 μm spot size. The detection laser had a wavelength of 532 nm, a spot size of 20 μm, and a power of 50 mW. Acoustic waveforms of surface displacement magnitude vs. time were measured at 80-μm steps along the flip chip surface by x-y raster scanning. The generation and detection laser spots were overlapped on the top surface. The scan area was 4.4 mm×4.4 mm in size. The frequencies of the generated ultrasonic waves ranged from 1 to 10 MHz, corresponding to 8 to 0.8 mm wavelengths. The resolution attained was less than 100 μm, which is nearly an order of magnitude smaller than the shortest ultrasonic wavelength. A resolution of about 20 μm should be attainable by use of optimized time gating and very small generation and detection laser spot sizes.

The preferred embodiments of this invention have been illustrated and described above. Modifications and additional embodiments, however, will undoubtedly be apparent to those skilled in the art. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

We claim:

1. A laser-ultrasonic method for detecting a defect in an attachment between a flip chip and a substrate, comprising the steps of:
    generating a probe acoustic wave within the flip chip by directing a generation laser beam to a predetermined generation spot on the top surface of the flip chip;
    detecting a reflected acoustic waveform via an interferometer and a detection laser beam that impinges the top surface of the flip chip at a detection spot having a predetermined spatial relationship to the generation spot;
    repeating said step of generating and said step of detecting for a plurality of predetermined generation and detection spots on the top surface of the flip chip; and
    comparing the reflected acoustic waveforms detected for at least two predetermined detection spots to detect the defect in the attachment between the flip chip and the substrate.

2. The method of claim 1, wherein the attachment is an underfill between the bottom of the flip chip and the substrate.

3. The method of claim 1, wherein the attachment is an area array of solder balls between contact pads on the flip chip and contact pads on the substrate.

4. The method of claim 1, wherein the defect is a void.

5. The method of claim 1, wherein the defect is a solder ball of insufficient mass.

6. The method of claim 1, wherein the flip chip comprises a semiconductor material selected from the group consisting of silicon, germanium, gallium arsenide, indium phosphide, and silicon carbide.

7. The method of claim 1, wherein the wavelength of the generation laser beam is predetermined such that the photon energy of the generation laser light exceeds the bandgap energy of the semiconductor material comprising the flip chip.

8. The method of claim 1, wherein the wavelength of the generation laser beam is predetermined such that the generation laser light is absorbed in the bulk of the semiconductor material comprising the flip chip.

9. The method of claim 1, wherein the wavelength of the detection laser beam is predetermined such that the photon energy of the detection laser light exceeds the bandgap energy of the semiconductor material comprising the flip chip.

10. The method of claim 1, wherein the flip chip comprises silicon and the wavelengths of the generation laser beam and the detection laser beam are both 532 nm.

11. The method of claim 1, wherein the flip chip comprises silicon and the wavelength of the generation laser beam is 532 nm and the wavelength of the detection laser beam is 515 nm.

12. The method of claim 1, wherein the flip chip comprises silicon and the wavelength of the generation laser beam is 1064 nm and the wavelength of the detection laser beam is 532 nm.

13. The method of claim 1, wherein the substrate comprises a ceramic material.

14. The method of claim 1, wherein the substrate comprises a polymer-based material.

15. The method of claim 1, wherein the diameter of the generation laser spot is 100 μm or less.

16. The method of claim 1, wherein the diameter of the detection laser spot is 100 μm or less.

17. The method of claim 1, wherein the distance between the center of the generation laser spot and the center of the detection laser spot is less than 300 μm.

18. The method of claim 1, wherein the top surface of the flip chip is x-y raster scanned with respect to the generation and detection laser beam spots.

19. The method of claim 1, wherein the time frame for the compared waveforms is limited to the time required for the first longitudinal wave reflection to reach the detection spot.

* * * * *